(12) United States Patent
Clay (10) Patent No.: US 9,074,967 B2
(45) Date of Patent: Jul. 7, 2015

(54) APPARATUS AND SYSTEM FOR SAMPLING AND SUPPLYING A FLUID TO AN ANALYZER

(71) Applicant: General Electric Company, Schenectady, NY (US)

(72) Inventor: Brian Keith Clay, Erie, CO (US)

(73) Assignee: General Electric Company, Schenectady, NY (US)

( * ) Notice: Subject to any disclaimer, the term of this patent is extended or adjusted under 35 U.S.C. 154(b) by 162 days.

(21) Appl. No.: 13/722,166

(22) Filed: Dec. 20, 2012

(65) Prior Publication Data

US 2014/0174207 A1    Jun. 26, 2014

(51) Int. Cl.
*G01N 1/16* (2006.01)
*G01N 1/10* (2006.01)
*G01N 1/20* (2006.01)
*G01N 35/10* (2006.01)

(52) U.S. Cl.
CPC .. *G01N 1/10* (2013.01); *G01N 1/20* (2013.01); *G01N 35/1079* (2013.01)

(58) Field of Classification Search
USPC ...................................................... 73/863.33
See application file for complete search history.

(56) References Cited

U.S. PATENT DOCUMENTS

| | | | |
|---|---|---|---|
| 4,442,720 A | | 4/1984 | Apley et al. |
| 4,566,342 A | * | 1/1986 | Kurz ........................... 73/863.03 |
| 4,624,150 A | | 11/1986 | Shimizu |
| 5,441,071 A | | 8/1995 | Doherty et al. |
| 5,976,468 A | | 11/1999 | Godec et al. |
| 6,271,043 B1 | | 8/2001 | Godec |
| 7,247,498 B2 | | 7/2007 | Godec |
| 8,196,479 B2 | * | 6/2012 | Ludwick et al. ............. 73/863.31 |
| 2005/0217351 A1 | * | 10/2005 | Kreck et al. .................. 73/64.56 |
| 2009/0223309 A1 | * | 9/2009 | Kurz ............................ 73/863.03 |

OTHER PUBLICATIONS

International Search Report and Written Opinion issued in connection with corresponding PCT Application No. PCT/US2013/071832 on Mar. 11, 2014.

* cited by examiner

*Primary Examiner* — Robert R Raevis
(74) *Attorney, Agent, or Firm* — Meunier Carlin & Curfman LLC (57) ABSTRACT

Apparatuses and systems for sampling fluid and providing fluid to an analyzer are provided. In an embodiment, a sampler may have a state switch for the housing cover. In another embodiment, multiple fluid streams may be housed in a single housing.

14 Claims, 7 Drawing Sheets

APPARATUS AND SYSTEM FOR SAMPLING AND SUPPLYING A FLUID TO AN ANALYZER

FIELD OF THE INVENTION

The subject matter disclosed herein relates to the field of chemical analysis, and more particularly to supplying a portion of fluid from a stream to a chemical analyzer.

BACKGROUND OF THE INVENTION

Fluid analysis is used in a wide variety of research, manufacturing, waste disposal and other applications. Typically, the fluid is transported from one location to another in a primary fluid stream, and it is often desirable to analyze the contents of the stream. This may be done by taking a sample from the primary fluid stream at selected time intervals. However, the composition of the fluid stream may vary considerably between the sampling intervals, so that the samples may not accurately reflect the composition of the stream. Generally, periodic testing of a small fraction of the total quantity of a stream is acceptable, so the majority of the fluid may bypass the analyzer.

Along with the fluid stream, it may be necessary to supply a known fluid sample to an analyzer from time to time to ensure that the analyzer is functioning properly or to calibrate the analyzer. This is done by observing whether the analyzer correctly analyzes the known sample. If the analyzer does not correctly identify the known sample, then the analyzer must be calibrated until it is operating within desired parameters. Of course, if the known sample does not in fact contain the precise composition that it is believed to contain, the analyzer will be incorrectly tested and calibrated. Therefore, the known sample should be delivered to the user in a controlled condition. A method of ensuring this is for the known sample to be prepackaged in small containers such as vials in the controlled environment of a facility specializing in such matters.

Most analyzers are equipped with a sampling mechanism (i.e. sampler) capable of introducing fluid samples into the analyzer from a single stream. Sites with multiple streams to be analyzed would require several analyzers, incurring high costs due to the general high price of analyzers.

BRIEF DESCRIPTION OF THE INVENTION

Disclosed herein are apparatuses and systems for sampling fluid and providing fluid to an analyzer. In an embodiment, a multiple stream sampler may include a first chamber comprising a first inlet for receiving a first online fluid stream and a second chamber comprising a second inlet for receiving a second online fluid stream, wherein the first chamber and the second chamber are within a single housing. The multiple stream sampler may also include a first sampling outlet fluidly connected with the first inlet, a second sampling outlet fluidly connected with the second inlet, and a discharge chamber fluidly connected with the first inlet and the second inlet.

In an embodiment, a system may comprise an analyzer and a multiple stream sampler, the multiple stream sampler may be connected with at least a first inlet for receiving a first fluid stream and a second inlet for receiving a second fluid stream, wherein the first inlet and second inlet are attached to a housing. The system may also include a valve fluidly connected with a first sampling outlet for a first sampling fluid stream and a second sampling outlet for a second sampling fluid stream, wherein the first sampling fluid stream is a portion of the first fluid stream, the second sampling fluid stream is a portion of the second fluid stream, and the valve is fluidly connected with the analyzer.

In an embodiment, a sampler may include a chamber for containing a stream of a first liquid, the chamber may include a liquid entrance, a liquid exit, and a first flow path between the entrance and exit and a sampling tube coupled to the chamber such that an inlet end of the sampling tube is in the first flow path inside the chamber and an outlet end of the sampling tube is outside the chamber. The sampler may also include a housing cover that covers a vial receptacle, and a housing cover position detector, wherein the detector is configured to detect the state of the housing cover.

This Brief Description of the Invention is provided to introduce a selection of concepts in a simplified form that are further described below in the Detailed Description. This Brief Description of the Invention is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

A more detailed understanding may be had from the following description, given by way of example in conjunction with the accompanying drawings wherein.

DETAILED DESCRIPTION OF THE INVENTION

As described herein in an embodiment, an integrated sampling device may connect to a plurality of online streams. In another embodiment, an integrated sampling device may have a housing cover position detector or vial position detector that may help control devices within a fluid stream analysis system which may include an analyzer, a sampler, and a valve.

Figures 1, 2, 3:
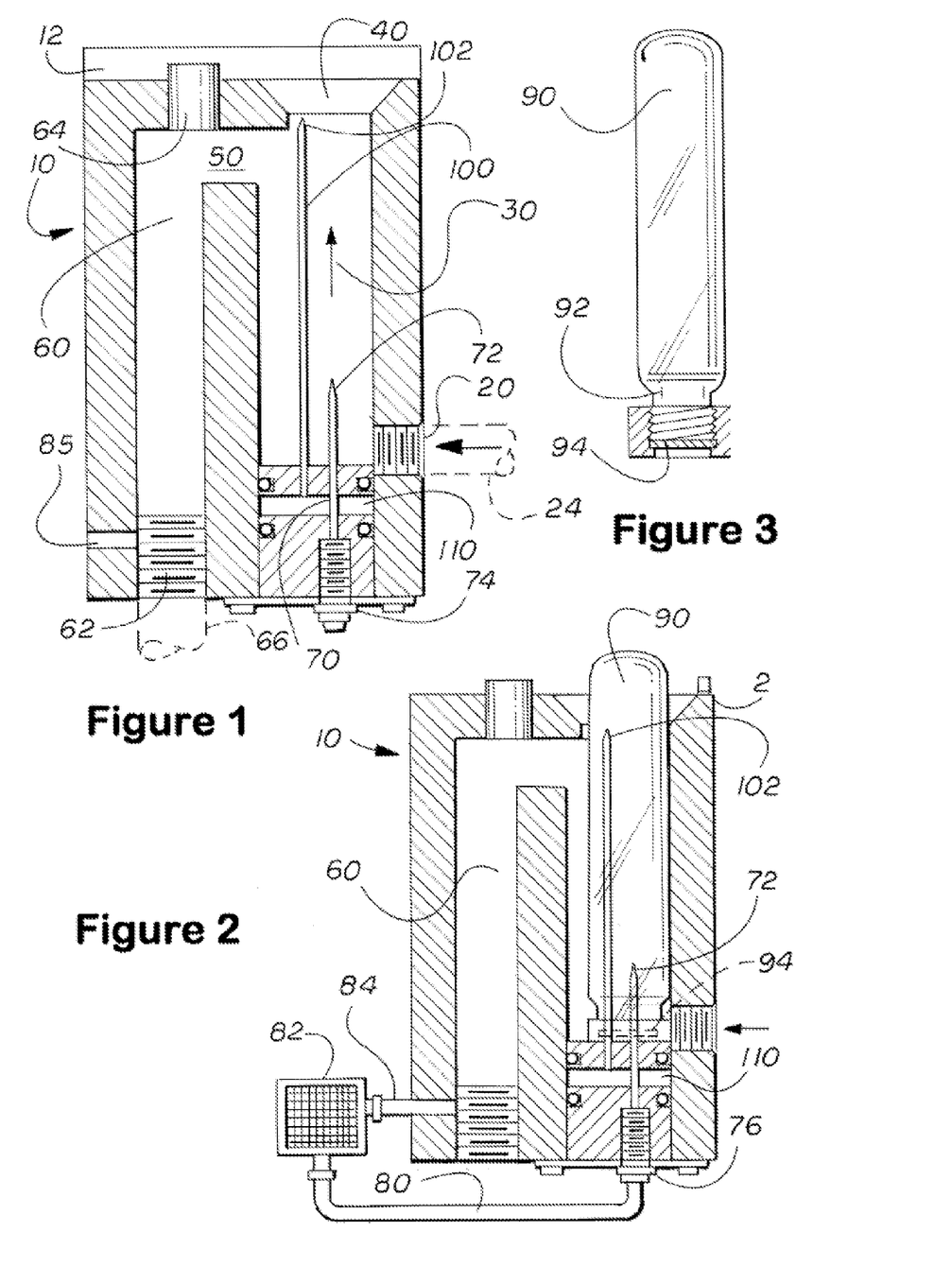
FIG. 1 is a view of a cross-section of a sampler.
FIG. 2 is a view of a partial cross-section of a sampler and a representative analyzer.
FIG. 3 is a side view of a vial.

FIG. 1 includes an integrated online sampler 10 (sampler) having an online stream fluid inlet 20 through which fluid may be introduced from an exterior intake conduit 24. The inlet 20 leads to a sampling chamber 30 that extends through the sampler 10 substantially along one side of the sampler 10. The sampling chamber 30 continues towards the top of the sampler 10 to a vial receptacle 40 that leads to the sampler 10 exterior. Beneath the vial receptacle 40, a horizontal weir 50 runs perpendicular from the sampling chamber 30. The horizontal weir 50 extends towards the opposite side of the sampler 10 from the sampling chamber 30, and connects to a discharge chamber 60. The discharge chamber 60 runs parallel to the sampling chamber 30, and terminates at the bottom of the sampler 10 at a discharge outlet 62 and terminates at the top of the housing of the sampler 10 at an overflow outlet 64. An external discharge conduit 66 may be attached to the discharge outlet 62. In an alternative embodiment, there is no discharge chamber, but the discharge outlet is directly in the sampling chamber 30.

The sampler 10 may be an integrated unit, wherein the above described chambers could be formed from either a single piece of conduit or from separate conduits joined together. The integrated unit, in which the separate chambers are bored through an otherwise substantially solid piece of material, provides strong and leak-proof chambers. The rectangular shape of the sampler 10 may be modified to almost any shape. A rectangular shape generally allows for the sampler 10 to be mounted to a flat surface.

A removable housing cover 12 for sampler 10 is attached to the top of the sampler 10, and covers the vial receptacle 40. The housing cover 12 partially covers the overflow outlet 64, so that the overflow outlet 64 is covered from above by the housing cover 12 but is open at a side at the interface between the sampler 10 and the housing cover 12. With the housing cover 12 placed on the sampler 10, fluid may flow through the sampler 10 in a circuit starting at the inlet 20, through the sampling chamber 30, across the horizontal weir 50, and through the discharge chamber 60 to the discharge outlet 62 and external discharge conduit 66. The fluid stream will not normally be at sufficient pressure to exit the sampler 10 through the overflow outlet 64. The overflow outlet 64 may allow fluid to escape should the pressure reach a predetermined threshold level.

A conduit, preferably a sampling needle 70, is positioned within the sampling chamber 30, with an inlet 72 proximate the top of the sampling needle 70. Preferably, the inlet 72 is positioned so as to pierce the septum (not shown). The sampling needle 70 continues beneath the sampling chamber 30 to the bottom of the housing of the sampler 10, where the sampling needle 70 terminates at a sampling outlet 76. Referring to FIG. 2, a sampling conduit 80 may be connected with the sampling outlet 76, and may run to a chemical analyzer 82 (e.g., total organic carbon concentration (TOC)) or other desired sampling apparatus. Alternatively, depending on the analyzer 82, the analyzer 82 may be directly connected with the sampling outlet 76. In either case, when fluid is flowing through the sampler 10 from the inlet 20 to the discharge outlet 62, an amount of fluid will be diverted through the sampling needle 70 to the analyzer 82. The amount of fluid diverted will typically be a small fraction of the total amount of fluid entering the inlet 20.

The analyzer 82 contains a discharge conduit 84 in fluid communication with the discharge chamber 60 via an analyzer waste inlet 85, so that all of the fluid will be commingled for manufacturing use, disposal, or other downstream application. In some applications, however, the analyzer 82 may alter the fluid during the analyzing process, and it may not be desirable to reintroduce that fluid into the primary fluid stream that is not diverted to the analyzer 82. Of course, a separate disposal system may be attached to the analyzer 82 in such situations.

Interposed within a fluid stream as described above, the sampler 10 allows for a constant sample of the fluid stream to be analyzed with minimal disruption to the primary stream flow. The constant flow to the analyzer 82 allows for the contents of the fluid stream to be analyzed as often as desired, such as on a periodic basis, or even continuously, as determined by the operation of the analyzer 82.

Sampler 10 may allow for a sample of known chemical composition and concentration to be supplied to the analyzer 82. This is useful so that the integrity of the analyzer 82 may be monitored by verifying that the known chemical is correctly analyzed. If the analyzer 82 analyzes the known chemical sample within acceptable limits, the normal fluid stream flow through the inlet 20 may be resumed. If the analyzer 82 does not analyze the known sample within acceptable limits, the analyzer 82 may be calibrated until the known chemical is correctly analyzed. The fluid stream is analyzed, and a known sample is analyzed, without changes to the plumbing configuration or the need for any tools to accomplish the change, and without employing any moving parts. Also, the configuration of the device ensures that the known sample passes through the same inlets and conduits as the fluid stream, thereby avoiding the inaccuracy and imprecision that may result from valves or tubing sections which are unique to the known sample or to the fluid stream.

Referring to FIGS. 2 and 3, the known chemical is preferably supplied in a sealed vial 90 that may be inserted into the sampling chamber 30 through the vial receptacle 40. To access the vial receptacle 40, the housing cover 12 is opened, exposing the vial receptacle 40. The mouth 92 of the vial 90 is sealingly covered by an inert frangible elastomeric diaphragm 94, which may be made of silicone or other materials. The inert frangible elastomeric diaphragm 94 allows a fluid sample of known composition and concentration to be supplied to a user in a controlled condition. Venting needle 100 may be used to supply air to the vial 90 to prevent the formation of a vacuum in the vial 90 as fluid drains out of the vial 90. Otherwise, the low pressure volume that would form in the end of the vial 90 opposite the mouth 92 as the known chemical exits the vial would disrupt the smooth fluid flow from the vial 90. Air or other gas is supplied into the vial 90 through the venting needle 100 at a venting needle inlet 102 located proximate the end of the venting needle 100 that extends above the sampling chamber 30. In an alternative embodiment, the venting needle 100 extends out the bottom of the housing and is connected via a conduit to the discharge chamber 60 or to other replacement fluid sources. The end of the venting needle 100 opposite the venting needle inlet 102 extends into a venting chamber 110 located beneath the sampling chamber 30.

The state of housing cover position switch 2 (e.g., open circuit or closed circuit) may be used to determine the position of housing cover 12 and also may be used in the operation of analyzer 82. In an embodiment, there may be a housing cover position switch 2 connected with the top of sampler 10, as shown in FIG. 2. Housing cover position switch 2 may be depressed when housing cover 12 is closed.

Figure 4:
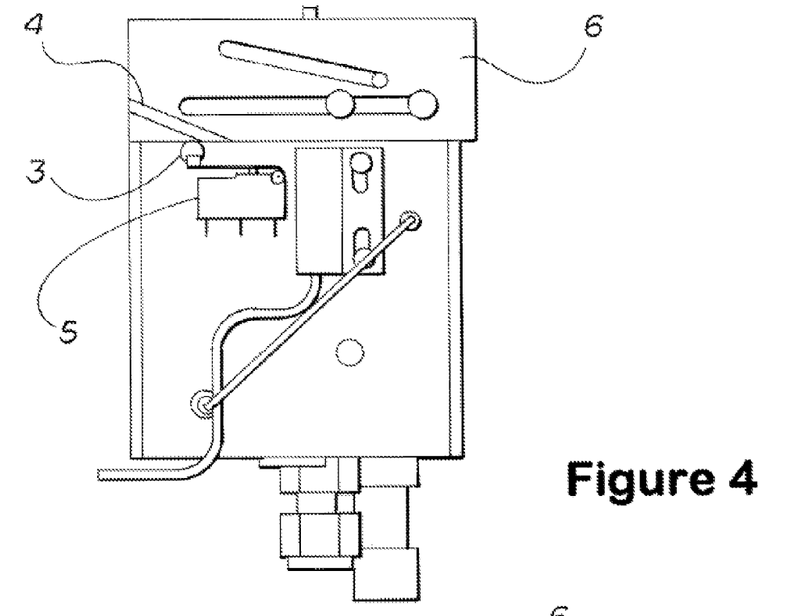
FIG. 4 is a rear view of a sampler with a housing cover position detector.
Figure 5:
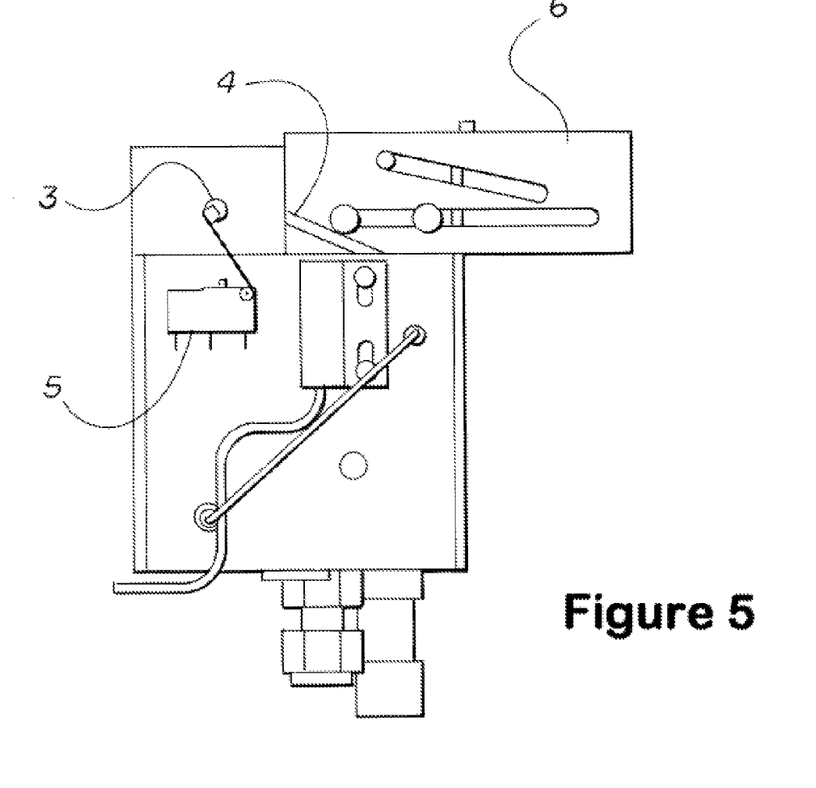
FIG. 5 is a rear view of a sampler with a housing cover position detector.

FIG. 4 and FIG. 5 display exemplary embodiments of a sampler with a housing cover position switch. FIG. 4 is an exemplary illustration of a one stream sampler where housing cover 6 is closed and housing cover position switch 3 is in a corresponding depressed position. FIG. 5 is an exemplary illustration of a one stream sampler where housing cover 6 is open and housing cover position switch 3 is in a corresponding raised position. In FIG. 4 and FIG. 5, housing cover 6 may slide along a horizontal axis to expose a vial receptacle (not shown), for example. Housing cover position switch 3 may be depressed when housing cover 6 is closed and may move upward when housing cover 6 slides open along the horizontal axis. Housing cover position switch 3 may have a wheel near the end in order to smoothly move up and down protruding ramp 4. Housing cover position switch 3 may be attached to a relay 5 that transmits the state of the housing cover position switch 3 to a communicatively connected with electromechanical valve, analyzer, a computing device, and the like.

Determining the status of a housing cover may be used to avoid improper modes. Referring to FIGS. 1 and 2, the attempt to sample from a vial 90 when housing cover 12 is closed, or the attempt to sample from an online stream when housing cover 12 is opened are exemplary improper modes. An online stream with a needle chamber for a vial receptacle may be sampled when the housing cover 12 is closed. When the housing cover 12 is open the system may expect a vial sample. Housing cover position switch 2 may prevent an error that may occur when a user intends to switch from online sampling to vial sampling, but does not open housing cover 12 and insert vial 90. In embodiments wherein the housing cover position is not determined, a user may turn off the supply fluid to the sampler's online stream fluid inlet 20, which may make the integral flow switch report no flow. The no flow condition is expected when housing cover 12 is opened, but, as previously stated, the housing cover 12 may still be closed.

In an embodiment with a housing cover position switch 2, analyzer 82 may be configured to analyze vial 90 when housing cover 12 is open (e.g., vial 90 is inserted). Housing cover position switch 2 may assist in avoiding the collection of bad data or other lost time/productivity due to an unknown status of housing cover 12 or vial 90 in sampler 10. Housing cover position switch 2 may add robustness to the data quality from analyzer 82 by preventing sampling of an empty sampling chamber 30 (vial chamber), for example. Any detector, such as a proximity sensor for housing cover 12 or vial 90 or a switch positioned and inserted near vial 90, may help avoid improper sampling and other related errors. The detector for the housing cover may be located near the area of the vial receptacle in order to specifically detect when the vial receptacle area is uncovered. In another embodiment, referring to FIG. 9 a housing cover position switch may be a momentary contact electrical switch that is depressed by a valve spool 139 (located within discharge chamber 136) that is pushed down when housing cover 144 is opened.

Figure 6:
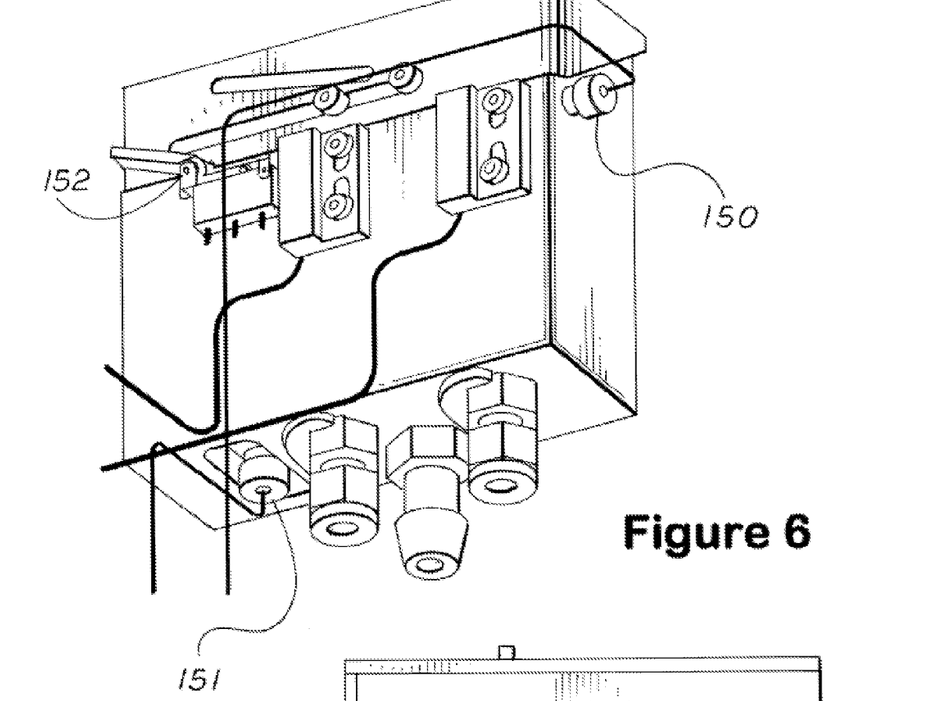
FIG. 6 is a perspective view of a 2-stream sampler.
Figure 7:
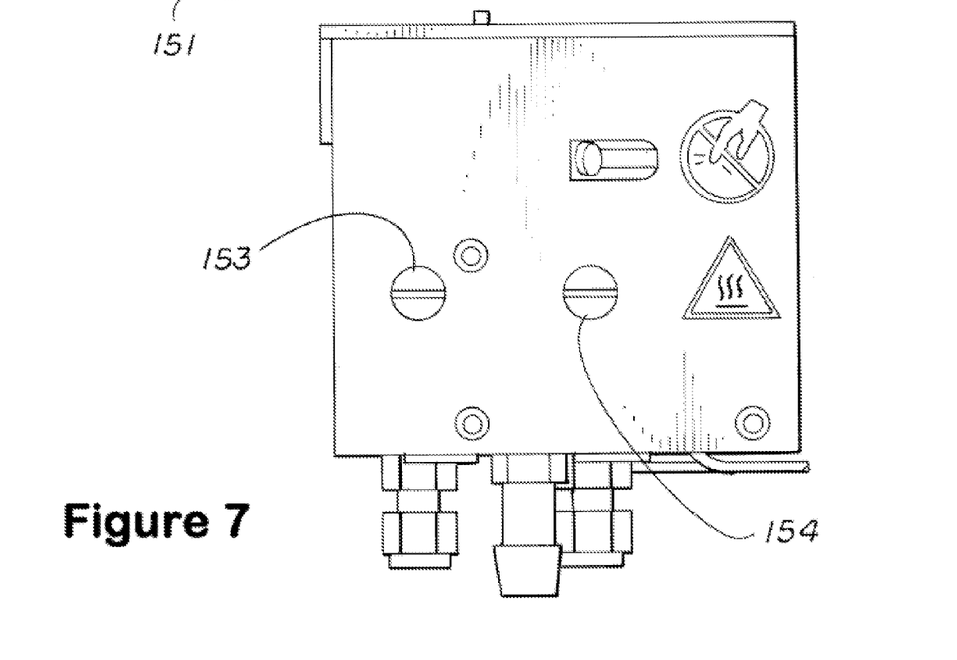
FIG. 7 is a front view of a 2-stream sampler.
Figure 8:
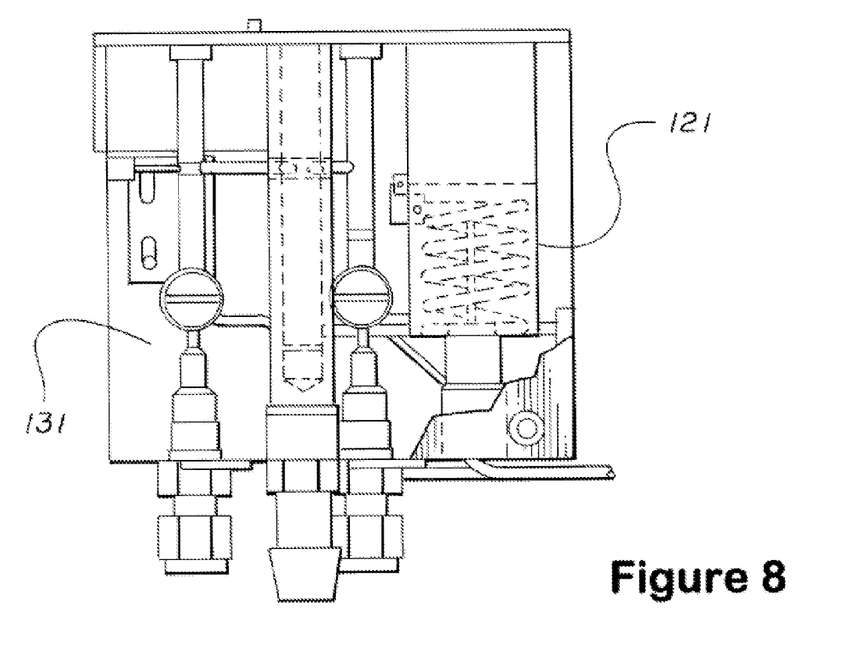
FIG. 8 is a transparent front view of a 2-stream sampler.

FIG. 6 is a rear perspective view of an integrated online sampler with two online streams. FIG. 6 shows a sampling outlet 151 for a needle chamber, a sampling outlet 150 for a chamber, and a housing cover position switch 152. FIG. 7 is a front view of an integrated online sampler with two online streams. In FIG. 7, the needle valve 153 and needle valve 154 are shown. FIG. 8 is a transparent front view of an integrated online sampler with two online streams, wherein one of the two streams may be sampled using a needle chamber 121.

Figure 9:
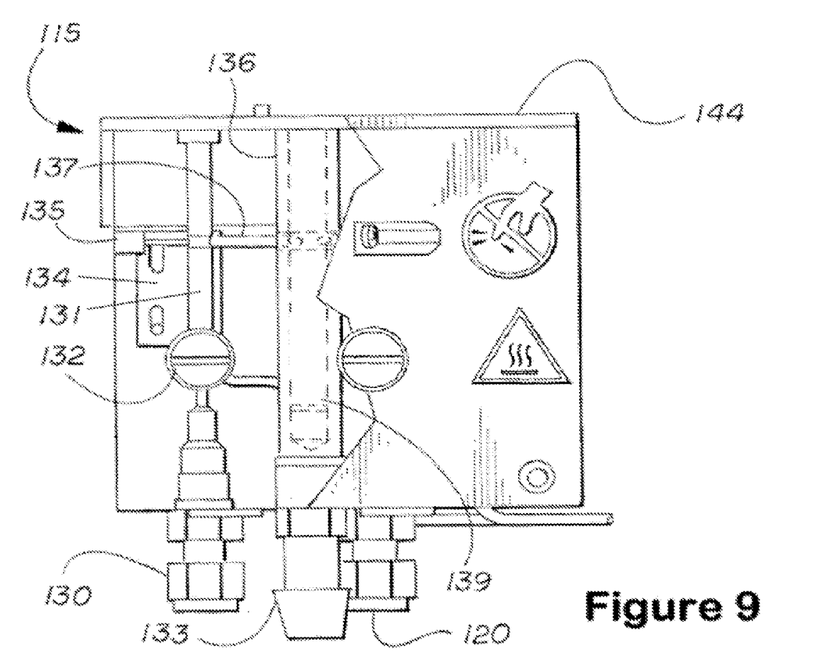
FIG. 9 is a partially transparent front view of a 2-stream sampler.

FIG. 9 is a front view of an online sampler 115 with two online streams, wherein the online sampler is partially transparent. Inlet 120 may fluidly connect to a needle chamber 121. Inlet 120 and inlet 130 may be attached to the online sampler 115 and direct streams of a fluid (e.g., water) that may be sourced from different fluid sources. The fluid streams from inlet 120 and inlet 130 may be fluidly isolated before and during sampling. The fluid streams may be combined when entering discharge chamber 136. Fluid streams from inlet 120 and inlet 130 may be contained in the same rectangular housing and may share a housing cover 144. Housing cover 144 may have a housing cover position switch (not shown) to determine the position of housing cover 144.

A fluid stream may flow through inlet 130, into a needle valve 132. The needle valve 132 may be used to adjust the flow rate. After flowing through the needle valve 132, the fluid may flow through conduit 131 and pass magnetic switch 134 which may verify the existence of a flow. After the fluid stream flows though conduit 131 a portion of the fluid is directed to sampling outlet 135, while a portion of the fluid is directed to discharge conduit 137 which leads to discharge chamber 136 and a discharge outlet 133. Fluid from needle chamber 121 may also eventually flow through discharge chamber 136 and discharge outlet 133. The fluid that flows through discharge outlet 133 may be discarded or may be used in another process.

Figure 10:
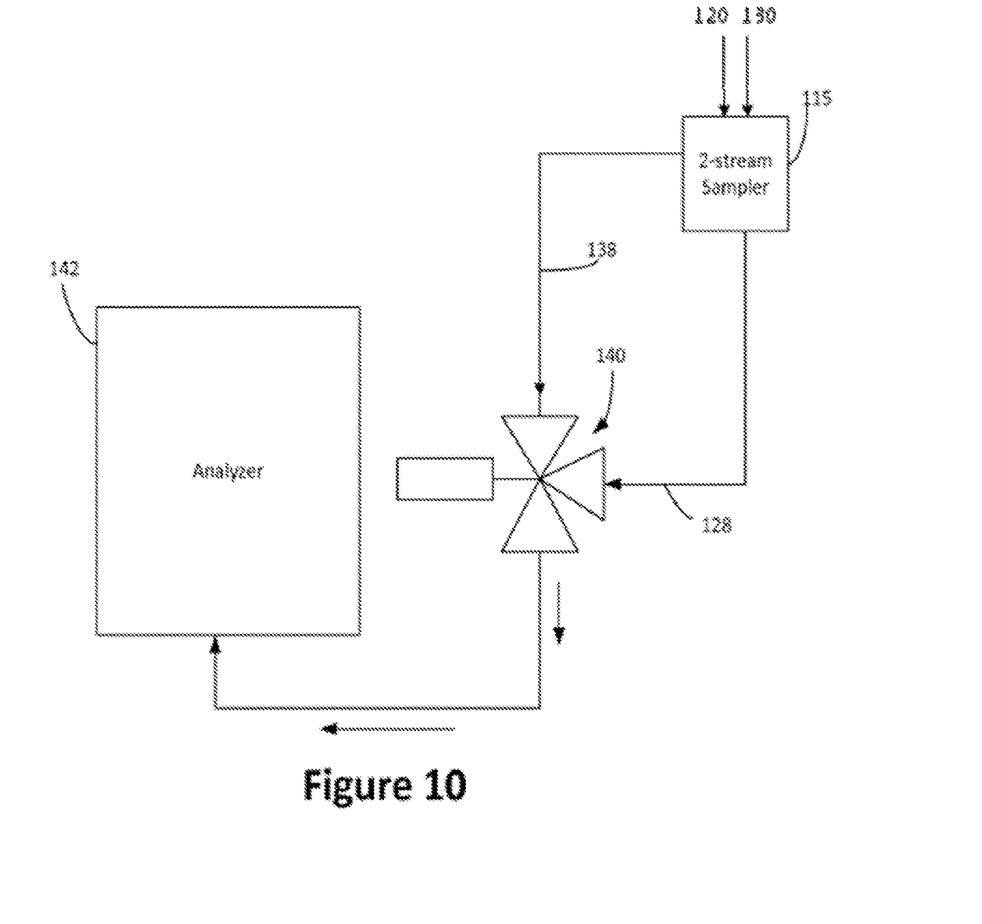
FIG. 10 is a block diagram of a 2-stream sampler and analyzer system.

FIG. 10 is an exemplary block diagram of a three-way valve 140 connected with an analyzer 142 and online sampler 115. The fluid streams of online sampler 115 may flow through respective sampling outlets and sampling conduits. The needle chamber 121 may have a sampling outlet that is fluidly connected with sampling conduit 128 and may allow an amount of fluid sourced from inlet 120 to be diverted to three-way valve 140. Sampling outlet 135 may be fluidly connected with sampling conduit 138 and may allow an amount of fluid sourced from inlet 130 to be diverted to three-way valve 140. Three-way valve 140 may be fluidly connected with analyzer 142. Three-way valve 140 may be configured so that only one stream at a time (e.g., either a stream from sampling conduit 128 or a stream from sampling conduit 138) is sampled by analyzer 142. A housing cover position switch may also be used in the operation of online sampler 115, three-way valve 140, or analyzer 142. In an embodiment, a housing cover position switch may indicate that housing cover 144 is open which may cause the three-way valve 140 to automatically allow sampling conduit 138 to be fluidly connected with analyzer 142.

Components included in online sampler 115 and the components connected thereto may be connected with a processor and other devices which may allow the state of different components to be analyzed and changed. For example, three-way valve 140 may be an electromechanical device that may be manipulated to direct a flow to analyzer 142 for testing based on the state of a fluid stream (e.g., a fluid stream through conduit 131). The state of the fluid streams, such as the amount of fluid or flow, may be detected using a magnetic sensor or other detector.

Without in any way limiting the scope, interpretation, or application of the claims appearing herein, embodiments disclosed herein provide multiple online fluid stream analysis capability. For example, the 2-stream capability described herein may enable one TOC analyzer to alternately monitor two separate water streams in an online application. This may allow the same analyzer to compare water quality between the upstream and downstream portions of a water purification system, for example. This reduces the number of TOC analyzers required in a facility with multiple online sample streams that need to have TOC monitored. The sampler allows for sampling multiple online fluid streams along with vial samples from the same device. In addition, a housing cover position switch and/or a vial position switch may allow for the control of an analyzer or other devices and reduce errors in the analysis of sampled fluids.

Figure 11:
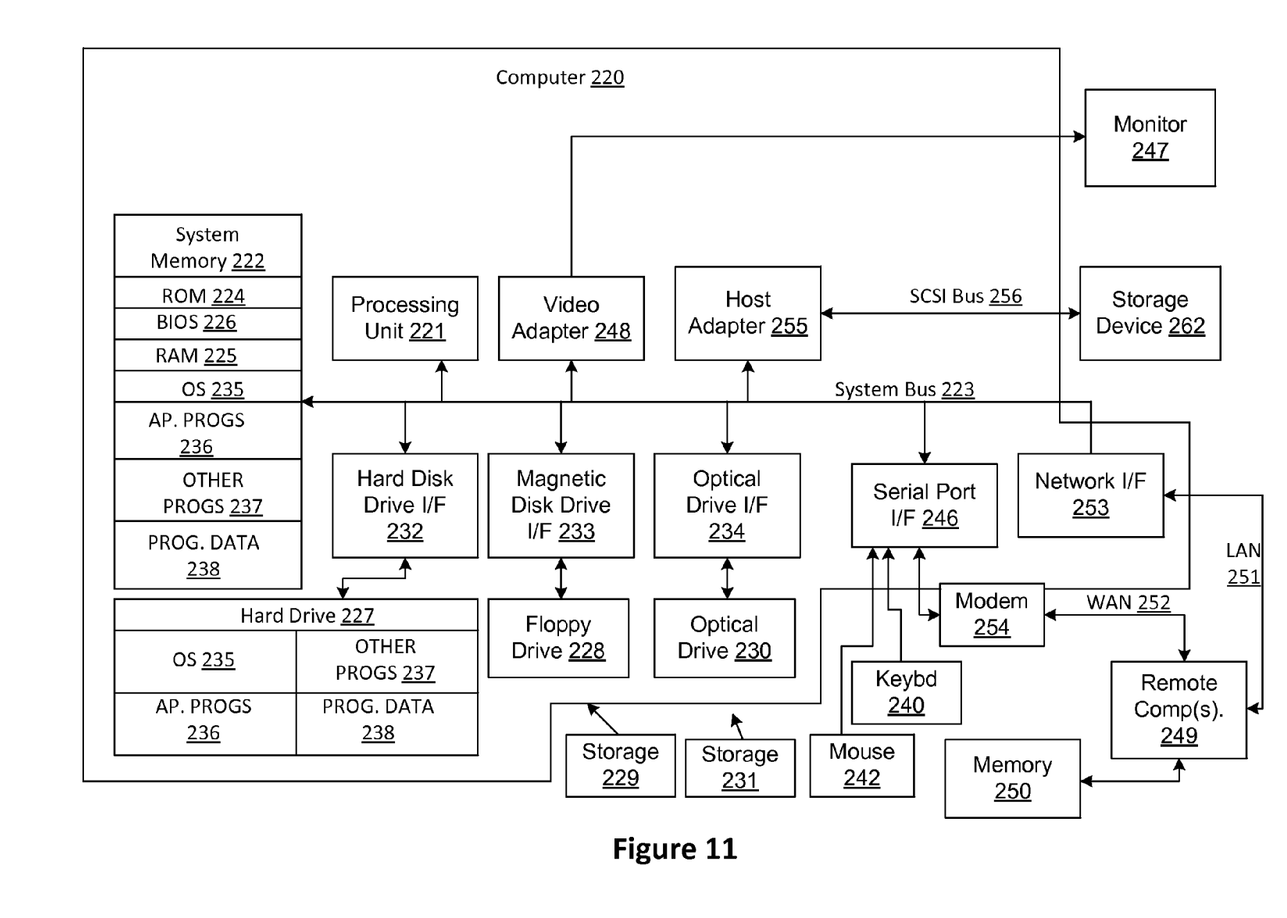
FIG. 11 is an exemplary block diagram representing a general purpose computer system in which aspects of the apparatuses and systems disclosed herein or portions thereof may be incorporated.

FIG. 11 and the following discussion are intended to provide a brief general description of a suitable computing environment in which the apparatuses, methods, and systems disclosed herein and/or portions thereof may be implemented. Although not required, the portions of apparatuses, methods, and systems herein are described in the general context of computer-executable instructions, such as program modules, being executed by a computer, such as a client workstation, server or personal computer. Generally, program modules include routines, programs, objects, components, data structures and the like that perform particular tasks or implement particular abstract data types. Moreover, it should be appreciated that portions of apparatuses, methods, and systems disclosed may be practiced with other computer system configurations, including hand-held devices, multi-processor systems, microprocessor-based or programmable consumer electronics, network PCs, minicomputers, mainframe computers and the like. The portions of apparatuses, methods, and systems disclosed herein may also be practiced in distributed computing environments where tasks are performed by remote processing devices that are linked through a communications network. In a distributed computing environment, program modules may be located in both local and remote memory storage devices.

FIG. 11 is a block diagram representing a general purpose computer system in which aspects of apparatuses, methods, and systems may be incorporated. As shown, the exemplary general purpose computing system includes a computer 220 or the like, including a processing unit 221, a system memory 222, and a system bus 223 that couples various system components including the system memory to the processing unit 221. The system bus 223 may be any of several types of bus structures including a memory bus or memory controller, a peripheral bus, and a local bus using any of a variety of bus architectures. The system memory includes read-only memory (ROM) 224 and random access memory (RAM) 225. A basic input/output system 226 (BIOS), containing the basic routines that help to transfer information between elements within the computer 220, such as during start-up, is stored in ROM 224.

The computer 220 may further include a hard disk drive 227 for reading from and writing to a hard disk (not shown), a magnetic disk drive 228 for reading from or writing to a removable magnetic disk 229, and an optical disk drive 230 for reading from or writing to a removable optical disk 231 such as a CD-ROM or other optical media. The hard disk drive 227, magnetic disk drive 228, and optical disk drive 230 are connected with the system bus 223 by a hard disk drive interface 232, a magnetic disk drive interface 233, and an optical drive interface 234, respectively. The drives and their associated computer-readable media provide non-volatile storage of computer readable instructions, data structures, program modules and other data for the computer 220. As described herein, computer-readable media is an article of manufacture and thus not a transient signal.

Although the exemplary environment described herein employs a hard disk, a removable magnetic disk 229, and a removable optical disk 231, it should be appreciated that other types of computer readable media which can store data that is accessible by a computer may also be used in the exemplary operating environment. Such other types of media include, but are not limited to, a magnetic cassette, a flash memory card, a digital video or versatile disk, a Bernoulli cartridge, a random access memory (RAM), a read-only memory (ROM), and the like.

A number of program modules may be stored on the hard disk, removable magnetic disk 229, removable optical disk 231, ROM 224 or RAM 225, including an operating system 235, one or more application programs 236, other program modules 237 and program data 238. A user may enter commands and information into the computer 220 through input devices such as a keyboard 240 and pointing device 242. Other input devices (not shown) may include a microphone, joystick, game pad, satellite disk, scanner, or the like. These and other input devices are often connected with the processing unit 221 through a serial port interface 246 that is coupled to the system bus, but may be connected by other interfaces, such as a parallel port, game port, or universal serial bus (USB). A monitor 247 or other type of display device is also connected with the system bus 223 via an interface, such as a video adapter 248. In addition to the monitor 247, a computer may include other peripheral output devices (not shown), such as speakers and printers. The exemplary system of FIG. 11 also includes a host adapter 255, a Small Computer System Interface (SCSI) bus 256, and an external storage device 262 connected with the SCSI bus 256.

The computer 220 may operate in a networked environment using logical connections to one or more remote computers, such as a remote computer 249. The remote computer 249 may be a personal computer, a server, a router, a network PC, a peer device or other common network node, and may include many or all of the elements described above relative to the computer 220, although only a memory storage device 250 has been illustrated in FIG. 11. The logical connections depicted in FIG. 11 include a local area network (LAN) 251 and a wide area network (WAN) 252. Such networking environments are commonplace in offices, enterprise-wide computer networks, intranets, and the Internet.

When used in a LAN networking environment, the computer 220 is connected with the LAN 251 through a network interface or adapter 253. When used in a WAN networking environment, the computer 220 may include a modem 254 or other means for establishing communications over the wide area network 252, such as the Internet. The modem 254, which may be internal or external, is connected with the system bus 223 via the serial port interface 246. In a networked environment, program modules depicted relative to the computer 220, or portions thereof, may be stored in the remote memory storage device. It will be appreciated that the network connections shown are exemplary and other means of establishing a communications link between the computers may be used.

Computer 220 may include a variety of computer readable storage media. Computer readable storage media can be any available media that can be accessed by computer 220 and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 220. Combinations of any of the above should also be included within the scope of computer readable media that may be used to store source code for implementing the methods and systems described herein. Any combination of the features or elements disclosed herein may be used in one or more embodiments.

In describing preferred embodiments of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

In describing preferred embodiments of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims. As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

What is claimed:

1. A multiple stream sampler comprising:
   a first inlet for receiving a first online fluid stream there through;
   a second inlet for receiving a second online fluid stream, wherein the first inlet and the second inlet are attached to a housing;
   a first sampling outlet, the first sampling outlet fluidly connected with the first inlet;
   a second sampling outlet, the second sampling outlet fluidly connected with the second inlet;
   a discharge chamber, the discharge chamber fluidly connected with the first inlet and the second inlet; and
   a vial detector attached to the housing, wherein the vial detector is configured to detect the presence of a vial in the multiple stream sampler.

2. The multiple stream sampler of claim 1, further comprising a housing cover for the housing, wherein the housing cover is configured to slide along a horizontal axis to open or close.

3. The multiple stream sampler of claim 1, further comprising:
   a housing cover for the housing; and
   a housing cover position detector, wherein the housing cover position detector is configured to detect a position of the housing cover.

4. The multiple stream sampler of claim 3, further comprising a relay communicatively connected with the housing cover position detector, the relay configured to communicate with a valve, wherein the valve fluidly connects the multi stream sampler with an analyzer.

5. The multiple stream sampler of claim 3, further comprising: a housing cover; and wherein the housing cover position detector is a housing cover position switch, and wherein the housing cover position switch is depressed by a valve spool.

6. The multiple stream sampler of claim 1, further comprising a vial receptacle within a first chamber, wherein the first chamber is fluidly connected with the first sampling outlet.

7. A system comprising:
   an analyzer;
   a multiple stream sampler, the multiple stream sampler connected with at least a first inlet for receiving a first fluid stream and a second inlet for receiving a second fluid stream, wherein the first inlet and second inlet are attached to a housing; and
   a valve fluidly connected with a first sampling outlet for a first sampling fluid stream and a second sampling outlet for a second sampling fluid stream, wherein the first sampling fluid stream is a portion of the first fluid stream, the second sampling fluid stream is a portion of the second fluid stream, and the valve is fluidly connected with the analyzer, and further comprising a vial detector attached to the housing, wherein the vial detector is configured to detect the presence of a vial in the multiple stream sampler.

8. The system of claim 7, further comprising:
   a housing cover positioned on an end of the housing; and
   a housing cover position detector attached to the housing, wherein the housing cover position detector is configured to detect a position of the housing cover of the multiple stream sampler.

9. The system of claim 8, further comprising:
   a processor communicatively connected with the analyzer; and
   a memory coupled to the processor, the memory having stored thereon executable instructions that when executed by the processor cause the processor to effectuate operations comprising:
   manipulating the analyzer based on a position of the housing cover.

10. The system of claim 8, further comprising:
    a processor communicatively connected with the valve; and
    a memory coupled to the processor, the memory having stored thereon executable instructions that when executed by the processor cause the processor to effectuate operations comprising:
    manipulating the valve based on a position of the housing cover.

11. The system of claim 8, wherein the housing cover position detector is located proximate to a vial receptacle.

12. The system of claim 8, wherein the housing cover position detector is a switch that comprises a wheel.

13. The system of claim 8, wherein the housing cover is configured to slide along a horizontal axis of the housing to open or close.

14. The system of claim 7, wherein the housing is rectangular.

* * * * *